United States Patent [19]
Lee et al.

[11] Patent Number: 5,955,457
[45] Date of Patent: Sep. 21, 1999

[54] WATER SOLUBLE RAPAMYCIN ESTERS

[75] Inventors: Hyuk-Koo Lee, Plattsburgh; Tianmin Zhu, Monroe, both of N.Y.

[73] Assignee: American Home Products Corporation, Madison, N.J.

[21] Appl. No.: 09/046,043

[22] Filed: Mar. 23, 1998

Related U.S. Application Data

[62] Division of application No. 08/763,768, Dec. 11, 1996, Pat. No. 5,780,462
[60] Provisional application No. 60/009,338, Dec. 27, 1995.

[51] Int. Cl.[6] .................................................. A61K 31/33
[52] U.S. Cl. ............................................................... 514/183
[58] Field of Search ............................................. 514/183

[56] References Cited

U.S. PATENT DOCUMENTS

| | | | |
|---|---|---|---|
| 3,929,992 | 12/1975 | Sehgal et al. . | |
| 3,993,749 | 11/1976 | Sehgal et al. . | |
| 4,316,885 | 2/1982 | Rakhit | 546/90 |
| 4,375,464 | 3/1983 | Sehgal et al. | 435/169 |
| 4,401,653 | 8/1983 | Eng . | |
| 4,650,803 | 3/1987 | Stella et al. | 514/291 |
| 4,885,171 | 12/1989 | Surendra et al. . | |
| 5,023,262 | 6/1991 | Caufield et al. | 540/456 |
| 5,023,263 | 6/1991 | Von Burg | 540/456 |
| 5,023,264 | 6/1991 | Caufield et al. | 540/456 |
| 5,078,999 | 1/1992 | Warner et al. | 514/291 |
| 5,080,899 | 1/1992 | Sturm et al. | 514/291 |
| 5,091,389 | 2/1992 | Ondeyka et al. | 540/256 |
| 5,100,883 | 3/1992 | Schiehser | 514/183 |
| 5,100,899 | 3/1992 | Calne | 514/291 |
| 5,102,876 | 4/1992 | Caufield | 514/183 |
| 5,118,677 | 6/1992 | Caufield | 514/183 |
| 5,118,678 | 6/1992 | Kao et al. | 514/183 |
| 5,120,842 | 6/1992 | Failli et al. | 514/63 |
| 5,130,307 | 7/1992 | Failli et al. | 514/183 |
| 5,138,051 | 8/1992 | Hughes et al. | 540/456 |
| 5,151,413 | 9/1992 | Caufield et al. | 514/63 |
| 5,169,851 | 12/1992 | Hughes et al. | 540/456 |
| 5,177,203 | 1/1993 | Failli et al. | 540/456 |
| 5,194,447 | 3/1993 | Kao | 540/456 |
| 5,221,670 | 6/1993 | Caufield | 514/183 |
| 5,233,036 | 8/1993 | Hughes | 540/455 |
| 5,258,389 | 11/1993 | Goulet et al. | 540/456 |
| 5,260,300 | 11/1993 | Hu | 540/456 |
| 5,302,584 | 4/1994 | Kao et al. | 540/456 |
| 5,321,009 | 6/1994 | Baeder et al. | 514/4 |
| 5,362,718 | 11/1994 | Skotnicki et al. | 540/450 |
| 5,378,696 | 1/1995 | Caulfield | 514/183 |
| 5,385,908 | 1/1995 | Nelson et al. | 540/406 |
| 5,385,909 | 1/1995 | Nelson et al. | 540/456 |
| 5,385,910 | 1/1995 | Ocain et al. | 540/456 |
| 5,387,589 | 2/1995 | Kulkarni | 514/291 |
| 5,389,639 | 2/1995 | Failli et al. | 540/456 |
| 5,391,730 | 2/1995 | Skotnicki et al. | 540/450 |
| 5,463,048 | 10/1995 | Skotnicki et al. | 540/456 |
| 5,491,231 | 2/1996 | Nelson et al. | 540/456 |
| 5,496,832 | 3/1996 | Armstrong | 514/291 |
| 5,516,770 | 5/1996 | Waranis et al. | 514/183 |
| 5,516,781 | 5/1996 | Morris et al. | 514/291 |

FOREIGN PATENT DOCUMENTS

| | | |
|---|---|---|
| 507555A1 | 10/1992 | European Pat. Off. . |
| 525960A1 | 2/1993 | European Pat. Off. . |
| 532862A1 | 3/1993 | European Pat. Off. . |
| WO9409010 | 9/1993 | WIPO . |

OTHER PUBLICATIONS

Venzina, C., J. Antibiot. 28:721 (1975).
Sehgal, S.N., J. Antibiot. 28:727 (1975).
Baker, H.J., Antibiot. 31:539 (1978).
Martel, R.R., Can. J. Physiol. Pharmacol. 55:48 (1977).
Staruch, M.J., FASEB 3:3411 (1989).
Dumont, F.J., FASEB 3:5256 (1989).
Calne, R.Y., Lancet 1183 (1978).
Morris, R.E., Med. Sci. Res. 17:877 (1989).
Baeder, W.L., Fifth Int. Conf. Inflamm. Res. Assoc. 121 (Abstract) (1990).
Meiser, B.M., J. Heart Lung Transplant. 11 (pt. 2):197 (1992).
Stepkowski, S.M., Transplantation Proc. 23:507 (1991).

*Primary Examiner*—Donald G. Daus
*Attorney, Agent, or Firm*—Arnold S. Milowsky

[57] ABSTRACT

A compound of the structure

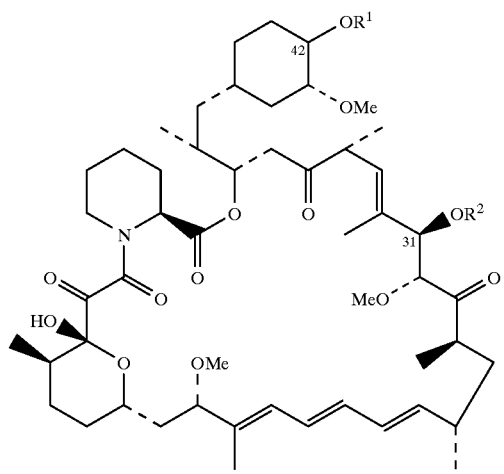

wherein $R^1$ and $R^2$ are each, independently, hydrogen or —$COCH_2$—S—$CH_2CH_2$—O—$CH_2$—($CH_2OCH_2$)$_n$—$CH_2$—O—$CH_2CH_2$—$OCH_3$; and n=8–450; with the proviso that $R^1$ and $R^2$ are not both hydrogen, which is useful as an immunosuppressive, antiinflammatory, antifungal, antiproliferative, and antitumor agent.

3 Claims, No Drawings

WATER SOLUBLE RAPAMYCIN ESTERS

This application claims the benefit of U.S. Provisional Application No. 60/009,338, filed Dec. 27, 1995 and is a division of application Ser. No. 08/763,768, filed Dec. 11, 1996, now U.S. Pat. No. 5,780,462.

BACKGROUND OF THE INVENTION

This invention relates to water soluble methoxypoly (ethylene glycol) esters of rapamycin and a method for using them for inducing immunosuppression, and in the treatment of transplantation rejection, graft vs. host disease, autoimmune diseases, diseases of inflammation, adult T-cell leukemia/lymphoma, solid tumors, fungal infections, and hyperproliferative vascular disorders.

Rapamycin is a macrocyclic triene antibiotic produced by *Streptomyces hygroscopicus*, which was found to have antifungal activity, particularly against *Candida albicans*, both in vitro and in vivo [C. Vezina et al., J. Antibiot. 28, 721 (1975); S. N. Sehgal et al., J. Antibiot. 28, 727 (1975); H. A. Baker et al., J. Antibiot. 31, 539 (1978); U.S. Pat. No. 3,929,992; and U.S. Pat. No. 3,993,749].

Rapamycin alone (U.S. Pat. No. 4,885,171) or in combination with picibanil (U.S. Pat. No. 4,401,653) has been shown to have antitumor activity. R. Martel et al. [Can. J. Physiol. Pharmacol. 55, 48 (1977)] disclosed that rapamycin is effective in the experimental allergic encephalomyelitis model, a model for multiple sclerosis; in the adjuvant arthritis model, a model for rheumatoid arthritis; and effectively inhibited the formation of IgE-like antibodies.

The immunosuppressive effects of rapamycin have been disclosed in FASEB 3, 3411 (1989). Cyclosporin A and FK-506, other macrocyclic molecules, also have been shown to be effective as immunosuppressive agents, therefore useful in preventing transplant rejection [FASEB 3, 3411 (1989); FASEB 3, 5256 (1989); R. Y. Calne et al., Lancet 1183 (1978); and U.S. Pat. No. 5,100,899].

Rapamycin has also been shown to be useful in preventing or treating systemic lupus erythematosus [U.S. Pat. No. 5,078,999], pulmonary inflammation [U.S. Pat. No. 5,080,899], insulin dependent diabetes mellitus [Fifth Int. Conf. Inflamm. Res. Assoc. 121 (Abstract), (1990)], smooth muscle cell proliferation and intimal thickening following vascular injury [Morris, R. J. Heart Lung Transplant 11 (pt. 2): 197 (1992)], adult T-cell leukemia/lymphoma [European Patent Application 525,960 A1], and ocular inflammation [European Patent Application 532,862 A1].

Mono- and diacylated derivatives of rapamycin (esterified at the 28 and 43 positions) have been shown to be useful as antifungal agents (U.S. Pat. No. 4,316,885) and used to make water soluble aminoacyl prodrugs of rapamycin (U.S. Pat. No. 4,650,803). Recently, the numbering convention for rapamycin has been changed; therefore according to Chemical Abstracts nomenclature, the esters described above would be at the 31- and 42-positions. U.S. Pat. No. 5,023,263 describes the preparation and use of 42-oxorapamycin and U.S. Pat. No. 5,023,264 describes the preparation and use of 27-oximes of rapamycin.

Polyethylene glycol (PEG) is a linear or branched, neutral polymer available in a variety of molecular weights and is soluble in water and most organic solvents. At molecular weights less than 1000 are the viscous, colorless liquids; higher molecular weight PEGs are waxy, white solids. The melting point of the solid is proportional to the molecular weight, approaching a plateau at 67° C. Molecular weights range from a few hundred to approximately 20,000 are commonly used in biological and biotechnological applications. Of much interest in the biomedical areas is the fact that PEG is nontoxic and was approved by FDA for internal consumption

DESCRIPTION OF THE INVENTION

This invent ion provides methoxypoly(ethylene glycol) esters of rapamycin having the structure

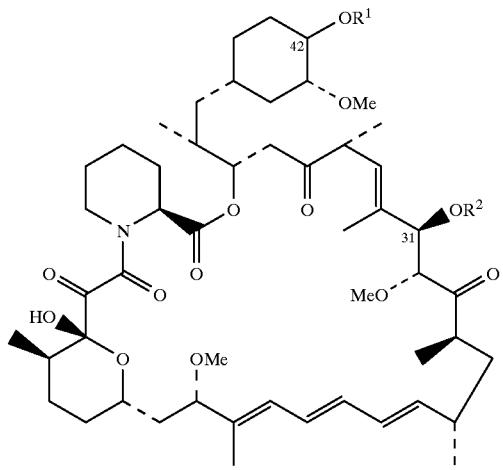

wherein $R^1$ and $R^2$ are each, independently, hydrogen or —$COCH_2$—S—$CH_2CH_2$—O—$CH_2$—$(CH_2OCH_2)_n$—$CH_2$—O—$CH_2CH_2$—$OCH_3$; and n=8–450;

with the proviso that $R^1$ and $R^2$ are not both hydrogen.

The compounds of this invention are water soluble prodrugs of rapamycin which are useful as immunosuppressive, antiinflammatory, antifungal, antiproliferative, and antitumor agents. Of the compounds of this invention, it is preferred that n=8–200; more preferred that n=8–135. Most preferred members are those in which n=8–20 and those in which n=90–120.

The compounds of this invention that are esterified at the 42- or 31,42-positions can be prepared by initially acylating the 42- or 31- and 42- positions of rapamycin with an acylating agent having the general structure X-$CH_2CO_2H$, where X is a suitable leaving group such as iodine, in the presence of a presence of a coupling reagent, such as dicyclohexylcarbodiimide (DCC) and a base such as dimethylaminopyridine (DMAP) to provide either a 42- or 31,42-acylated rapamycin having the following structure:

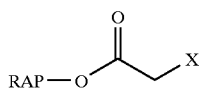

Mixtures of 42- and 31,42-esters can be separated by chromatography. Reaction of the acylated rapamycin with monomethoxypoly(ethylene glycol) thiol in the presence of a base such. as PROTON SPONGE ([1,8-(bis (dimethylamino)naphthalene, N,N,N'N'-tetramethyl-1,8-naphthalenediamine]) or sodium bicarbonate provides the desired 42- or 31,42- esters of this invention.

The 31-esters of this invention can be prepared by protecting the 42-alcohol of rapamycin with a protecting group, such as with a tert-butyl dimethylsilyl group, followed by esterification of the 31 -position by the procedures described above. The preparation of rapamycin 42-silyl ethers is described in U.S. Pat. No. 5,120,842, which is hereby incorporated by reference. Removal of the protecting group provides the 3 1-esterified compounds. In the case of the tert-butyl dimethylsilyl protecting group, deprotection can be accomplished under mildly acidic conditions, such as acetic acid/water/THF. The deprotection procedure is described in Example 15 of U.S. Pat. No. 5,118,678, which is hereby incorporated by reference.

Having the 31-position esterified and the 42-position deprotected, the 42-position can be esterified using a different acylating agent than was reacted with the 31-alcohol, to give compounds having different esters at the 31- and 42-positions. Alternatively, the 42-esterified compounds, prepared as described above, can be reacted with a different acylating agent to provide compounds having different esters at the 31- and 42-positions.

This invention also covers analogous esters of other rapamycins such as, but not limited to, 29-demethoxyrapamycin, [U.S. Pat. No. 4,375,464, 32-demethoxyrapamycin under C.A. nomenclature]; rapamycin derivatives in which the double bonds in the 1-, 3-, and/or 5-positions have been reduced [U.S. Pat. No. 5,023,262]; 29-desmethylrapamycin [U.S. Pat. No. 5,093,339, 32-desmethylrapamycin under C.A. nomenclature]; 7,29-bisdesmethylrapamycin [U.S. Pat. 5,093,338, 7,32-desmethylrapamycin under C.A. nomenclature]; 27-hydroxyrapamycin [U.S. Pat. No. 5,256,790] and 15-hydroxyrapamycin [U.S. Pat. No. 5,102,876]. This invention also covers esters at the 31-position of 42-oxorapamycin [U.S. Pat. No. 5,023,263]. The disclosures in the above cited U.S. patents are hereby incorporated by reference.

The reagents used in the preparation of the compounds of this invention can be either commercially obtained or can be prepared by standard procedures described in the literature.

Immunosuppressive activity for representative compounds of this invention was established in an in vivo pinch skin graft standard pharmacological test procedure that measures the immunosuppressive activity of the compound tested as well as the ability of the compound tested to inhibit or treat transplant rejection. The procedure for this standard pharmacological test procedure and results obtained are provided below.

Representative compounds of this invention were evaluated in an in vivo test procedure designed to determine the survival time of pinch skin graft from male BALB/c donors transplanted to male $C_3H$(H-2K) recipients. The method is adapted from Billingham R. E. and Medawar P. B., J. Exp. Biol. 28:385–402, (1951). Briefly, a pinch skin graft from the donor was grafted on the dorsum of the recipient as a allograft, and an isograft was used as control in the same region. The recipients were treated with either varying concentrations of test compounds intraperitoneally or orally. Rapamycin was used as a test control. Untreated recipients serve as rejection control. The graft was monitored daily and observations were recorded until the graft became dry arid formed a blackened scab. This was considered as the rejection day. The mean graft survival time (number of days ±S.D.) of the drug treatment group was compared with the control group. Results are expressed as the mean survival time in days. Untreated (control) pinch skin grafts are usually rejected within 6–7 days. A survival time of 11.67±0.63 days was obtained for rapamycin at 4 mg/kg, i.p. As the compounds of this invention are prodrugs of rapamycin the doses provided below are given in rapamycin equivalent doses (6.2 mg of the compound of Example 2 contains the equivalent of 1 mg rapamycin). The results obtained for the compound of Example 2, PEG-5000, and an untreated control group are provided in the table below.

| Compound | Dose* | Route | Survival Time (Mean ± S.E.) |
|---|---|---|---|
| Example 2 | 20 mg/kg | p.o. | 12.50 ± 0.22 |
| Example 2 | 5 mg/kg | p.o. | 11.33 ± 0.33 |
| Example 2 | 1.25 mg/kg | p.o. | 8.67 ± 0.21 |
| Example 2 | 4 mg/kg | i.p. | 12.67 ± 0.21 |
| Example 2 | 1 mg/kg | i.p. | 11.33 ± 0.21 |
| Example 2 | 0.25 mg/kg | i.p. | 9.5 ± 0.22 |
| Control | | | 7.00 ± 0.00 |
| PEG-5000 | | | 7.00 ± 0.00 |

*Doses of the compound of Example 2 are provided in rapamycin equivalent doses.

The results of this standard pharmacological test procedures demonstrate immunosuppressive activity for the compounds of this invention. Additionally, the results obtained in the skin graft test procedure demonstrates the ability of the compounds of this invention to treat or inhibit transplantation rejection.

Based on the results of these standard pharmacological test procedures, the compounds are useful in the treatment or inhibition of transplantation rejection such as kidney, heart, liver, lung, bone marrow, pancreas (islet cells), cornea, small bowel, and skin allografts, and heart valve xenografts; in the treatment or inhibition of graft vs. host disease; in the treatment or inhibition of autoimmune diseases such as lupus, rheumatoid arthritis, diabetes mellitus, myasthenia gravis, and multiple sclerosis; and diseases of inflammation such as psoriasis, dermatitis, eczema, seborrhea, inflammatory bowel disease, pulmonary inflammation (including asthma, chronic obstructive pulmonary disease, emphysema, acute respiratory distress syndrome, bronchitis, and the like), and eye uveitis.

Because of the activity profile obtained, the compounds of this invention also are considered to have antitumor, antifungal activities, and antiproliferative activities. The compounds of this invention therefore also useful in treating solid tumors, including sarcomas and carcinomas, such as astrocytomas, prostate cancer, breast cancer, small cell lung cancer, and ovarian cancer; adult T-cell leukemia/lymphoma; fungal infections; and hyperproliferative vascular diseases such as restenosis and atherosclerosis. When used for restenosis, it is preferred that the compounds of this invention are used to treat restenosis that occurs following an angioplasty procedure.

When used for this purpose, the compounds of this invention can be administered prior to the procedure, during the procedure, subsequent to the procedure, or any combination of the above.

When administered for the treatment or inhibition of the above disease states, the compounds of this invention can be administered to a mammal orally, parenterally, intranasally, intrabronchially, transdermally, topically, intravaginally, or rectally.

The compounds of this invention are particularly advantageous as immunosuppressive, an antiinflammatory, antifungal, antiproliferative, and antitumor agents because of their water solubility. For example, rapamycin has a solubility of 1.2 $\mu$g/mL in water, whereas the compound of Example 2 has a solubility of >100 mg/mL, thereby facilitating the ease of formulation and administration.

It is contemplated that when the compounds of this invention are used as an immunosuppressive or antiinflammatory agent, they can be administered in conjunction with one or more other immunoregulatory agents. Such other immunoregulatory agents include, but are not limited to azathioprine, corticosteroids, such as prednisone and methylprednisolone, cyclophosphamide, rapamycin, cyclosporin A, FK-506, OKT-3, and ATG. By combining the compounds of this invention with such other drugs or agents for inducing immunosuppression or treating inflammatory conditions, the lesser amounts of each of the agents are required to achieve the desired effect The basis for such combination therapy was established by Stepkowski whose results showed that the use of a combination of rapamycin and cyclosporin A at subtherapeutic doses significantly prolonged heart allograft survival time. [Transplantation Proc. 23: 507 (1991)].

The compounds of this invention can be formulated neat or with a pharmaceutical carrier to a mammal in need thereof. The pharmaceutical carrier may be solid or liquid.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, lethicins, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellant.

Liquid pharmaceutical compositions which are sterile solutions or suspensions can be utilized by, for example, intramuscular, intraperitoneal or subcutaneous injection. Sterile solutions can also be administered intravenously. The compound can also be administered orally either in liquid or solid composition form.

The compounds of this invention may be administered rectally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may also be administered transdermally through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semi-solid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semipermiable membrane covering a reservoir containing the active ingredient with or without a carrier, or a matrix containing the active ingredient. Other occlusive devices are known in the literature.

In addition, the compounds of this invention may be employed as a solution, cream, or lotion by formulation with pharmaceutically acceptable vehicles containing 0.1–5 percent, preferably 2%, of active compound which may be administered to a fungally affected area.

The dosage requirements vary with the particular compositions employed, the route of administration, the severity of the symptoms presented and the particular subject being treated. Based on the results obtained in the standard pharmacological test procedures, projected daily dosages of active compound would be 0.1 $\mu$kg–100 mg/kg, preferably between 0.001–25 mg/kg, and more preferably between 0.01–5 mg/kg. Treatment will generally be initiated with small dosages less than the optimum dose of the compound. Thereafter the dosage is increased until the optimum effect under the circumstances is reached; precise dosages for oral, parenteral, nasal, or intrabronchial administration will be determined by the administering physician based on experience with the individual subject treated. Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

The following examples illustrate the preparation and biological activities of representative compounds of this invention.

EXAMPLE 1

Rapamycin 42-iodoacetate ester

Rapamycin (0.5 g, $5.5 \times 10^{-4}$ mole) and DMAP (3.0 mg) were dissolved in 15 mL of anhydrous methylene chloride. Iodoacetic acid (0.123 g, $6.6 \times 10^{-4}$ mole) and DCC (0.136 g, $6.6 \times 10^{-4}$ mole) were dissolved in 20 mL of anhydrous methylene chloride and the mixture was transferred to a dropping funnel; this mixture was slowly added to the rapamycin solution over a period of 30 min with stirring. The reaction mixture was stirred at room temperature for one additional hour.

The resulting solution was filtered through a sintered glass filter. The filtrate was transferred to a separatory funnel and washed first with two 40 mL portions of sodium bicarbonate solution (5.5 g/100 mL) and next with water (2×50 mL). The methylene chloride layer was dried with 3 g of anhydrous sodium sulfate for 5 hours. Then the sodium sulfate was removed by filtration and methylene chloride was evaporated, yielding 0.53 g of a pale yellow solid compound. HPLC showed the presence of the 42-ester (55%), 31-ester (9.2%), 31,42-diester (17%), and unreacted rapamycin (17%).

The pure 42-iodoacetate was isolated by preparative HPLC on a Primesphere (250×50 mm, 10 micron) column. Rapamycin 42-iodoacetate eluted at 8.1 min with the use of 80% methylene chloride (solution A) and 20% solution B. Solution B consisted of 85% methylene chloride and 15% solution C (2:1=methanol:isopropanol).

The eluate was evaporated and the residue taken up in methylene chloride, dried and evaporated, yielding 0.206 g of a solid compound.

(+) Ion MS m/z 1099.5 $(M+NH_4)^+$; (-) Ion MS m/z 1080.5.

$^1$H NMR(400 MHz, DMSO-$d_6$) $\delta$5 3.78 (s, 2H, CO—$CH_2$—I), 4.54 (m, 1H, H-42).

Anal. Calcd for $C_{53}H_{80}NO_4I$: C, 58.83; H, 7.45; N, 1.29. Found: C, 58.97; H, 30 7.64; N, 1.36.

EXAMPLE 2
Rapamycin 42-ester with methoxypoly(ethylene glycol) thiol 5000
Method 1

Rapamycin 42-iodoacetate ester (0.1 g, $9.2 \times 10^{-5}$ mole) was dissolved in methylene chloride (15 mL) and methanol (15 mL). Then, mPEG-SH 5000 (0.6 g, $1.2 \times 10^{-4}$ mole) and PROTON SPONGE (20 mg, $9.3 \times 10^{-5}$ mole) were added to this reaction solution which was stirred at room temperature overnight. Then, 10 mg of PROTCON SPONGE was again added and the reaction solution was again stirred at room temperature overnight. The reaction was quenched by adding ether (200 mL). The white precipitate was filtered and washed with ether (3×20 mL), yielding 0.59 g crude product.

The crude product was further purified by preparative HPLC on a Zorbax C8 column (250×20 mm) using gradient solution A with 30–80% solution B. Solution A consisted of 90% 0.1 M TEAA (tetraethylammonium acetate) pH 4.5 buffer and 10% acetonitrile. Solution B consisted of 10% 0.1 M TEAA pH 4.5 buffer and 90% acetonitrile. Rapamycin 42-mPEG-S 5000 acetate ester eluted at 21 min. The aqueous phase was extracted with methylene chloride (2×50 mL). The organic layer was dried with anhydrous sodium sulfate for 14 hours, and concentrated to a volume of 10 mL under reduced pressure. The product was precipitated by adding 100 mL ether. The white precipitate was collected on a sintered glass filter and washed with ether (3–20 mL), yielding 109.6 mg of product.

Method 2

Rapamycin 42-iodoacetate ester (0.5 g, $4.6 \times 10^{-4}$ mole) was dissolved in 130 mL of solution containing 50% acetonitrile and 50% aqueous $NaHCO_3$ (0.1 M) solution. The solution was flushed with $N_2$ for 10 min. In order to check the initial reactant condition, 20 $\mu$L of sample was withdrawn and added to 1 mL of acetonitrile. The solution was filtered and 10 $\mu$L of the sample was subjected to HPLC analysis.

mPEG-SH 5000 ( 3.15 g, $6.3 \times 10^{-4}$ mole) was added to the reaction solution over a period of 1.5 h and the reaction stirred at room temperature for another 1.5 h. Another 20 $\mu$L of sample was withdrawn, mixed with 1 mL of acetonitrile, filtered and injected into the HPLC system. Results of HPLC analysis showed that rapamycin iodoacetate was quantitatively converted to rapamycin 42-mPEG-S 5000 acetate ester.

The reaction mixture was extracted with methylene chloride (2×500 mL). After the organic layer was dried with anhydrous $Na_2SO_4$ and filtered, the filtrate was concentrated to a volume of about 20 mL. The final crude product was precipitated by adding 250 mL ether; this slurry was then filtered and dried under vacuum, yielding 3.13 g of dry white material. The unreacted mPEG-SH was removed by preparative HPLC as described in Method 1.

MS (MADI/TOF) shows an average MW of 5877.47 for the product and 4923.66 for the starting mPEG-SH 5000. The difference in mass (953.81) exactly matched the rapamycin 42-acetate moiety (953.6). The ester side chain can be represented by the formula —$COCH_2$—S—$CH_2CH_2$—O—$CH_2$—$(CH_2OCH_2)_n$—$CH_2$—O—$CH_2CH_2$—$OCH_3$, where n is an average of 108 repeating units.

$^1$H NMR (400 MHz, CDCl3): $\delta$ 2.84 (t, 2H, S—$CH_2$—$CH_2$), 3.27 (s, 2H, CO—$CH_2$—S), 3.36 (s, 3H, —$OCH_3$), 3.64 (m, 4H, O—$CH_2$—$CH_2$—O), 4.69 (m, 1H, H-42).

MS (MALDI/TOF) m/z 5877.47 (ave. M. Wt.).

UV($CH_3CN$) $\lambda$max 268, 278, 290 nm.

EXAMPLE 3
Rapamycin 31,42-diiodoacetate

Rapamycin (0.5 g, $5.5 \times 10^{-4}$ mole), DCC (0.28 g, $1.4 \times 10^{-3}$ mol), and DMAP (30 mg) were dissolved in anhydrous methylene chloride (15 mL). Iodoacetic acid (0.25 g, $1.4 \times 10^{-3}$ mole) was added to the reaction solution, and reaction mixture was stirred for one hour at room temperature. Then, the solution was filtered through a sintered glass filter. The filtrate was washed with two 40 mL portions of sodium bicarbonate solution (5.5 g/100 mL) and with water (2×50 mL). The methylene chloride layer was dried with 3 g of anhydrous sodium sulfate for 5 h. Then, the sodium sulfate was removed by filtration and methylene chloride was evaporated, yielding 0.63 g of a pale yellow solid material. HPLC data indicated that 99.4% of rapamycin 31, 42-diiodoacetate was formed.

(+) Ion MS m/z 1272.3 $(M+Na)^+$.

$^1$H NMR (400 MHz, $CDCl_3$) $\delta$ 3.77 (q, 2H, CO—$CH_2$—31-ester), 3.784 (s, 2H, CO—$CH_2$—I, 42-ester), 4.31 (d, 1H, H-31), 4.54 (m, 1H, H-42).

EXAMPLE 4
Rapamycin 31,42-diester with methoxypoly(ethylene glycol) thiol 5000

Rapamycin 31,42-diiodoacetate (5.99 mg, $4.8 \times 10^{-5}$ mole) was dissolved in 70 ml of 50% $CH_3CN$— 50% $NaHCO_3$ (0.1 M) solution. The solution was purged with nitrogen for 10 min. mPEG-SH 5000 (0.778 g, $1.56 \times 10^{-4}$ mole) was added into the reaction solution. After the reaction solution was stirred for 30 min, 30 $\mu$L of sample was withdrawn, mixed with one mL of acetonitrile, and filtered. The sample (10 $\mu$L) was subjected to HPLC analysis. The data indicated that the rapamycin diiodoacetate was 100% converted to the rapamycin-31, 42-di(mPEG-S-5000 acetate) ester.

The reaction mixture was extracted with dry methylene chloride (2×300 mL). The methylene chloride layer was dried with anhydrous sodium sulfate and filtered. The filtrate was concentrated to a volume of 20 mL. The product was precipitated by adding 250 mL ether, filtered, and dried under the vacuum, yielding 0.22 g of white material.

MS (MALI/TOF) shows average M.Wt. 10983.6 Da. The ester side chains can be represented by the formula —$COCH_2$—S—$CH_2CH_2$—O—$CH_2$-$(CH_2OCH_2)_n$—$CH_2$—O—$CH_2CH_2$—$OCH_3$, where n is an average of 108 repeating units.

$^1$H NMR (400 MHz, $CDCl_3$) $\delta$ 3.23 (q, 2H, CO—$CH_2$—S, 3 1-ester), 3.25 (s, 2H, CO—$CH_2$—S, 42-ester), 4.65 (m, H, H-42), 5.25 (d, 1H, H-31).

EXAMPLE 5
Rapamycin 42-iodoacetate ester with metboxypoly(ethylene glycol) thiol 750

Rapamycin 42-iodoacetate ester (100 mg, $9.2 \times 10^{-5}$ mole) was dissolved in 30 mL solution of 50% $CH_3CN$—50%

NAHCO$_3$ (0.1 M) solution. The solution was purged with nitrogen for 10 min. mPEG-SH-750 (1.25 g, 1.67×10$^{-3}$ mole) was added into the reaction solution. After the reaction solution was stirred for 30 min, 30 μL of sample was withdrawn, added with one mL of CH$_3$CN and filtered. The sample (10 μL) was subjected to HPLC analysis. The data indicated that the rapamycin 42-iodoacetate was quantitatively converted to rapamycin 42-mPEG-S-750, acetate ester.

The reaction mixture was extracted with dry methylene chloride (2×300 mL). The methylene chloride layer was dried with anhydrous sodium sulfate and filtered. The filtrate was concentrated to a volume of 20 mL. The product was precipitated by adding 250 mL ether, filtered and dried under the vacuum, yielding 80 mg of a viscous oily liquid material.

The ester side chain can be represented by the formula —COCH$_2$—S—CH$_2$CH$_2$—O—CH$_2$—(CH$_2$OCH$_2$)$_n$—CH$_2$—O—CH$_2$CH$_2$—OCH$_3$, where n is an average of 14 repeating units.

ESI-MS (M+NH$_4$)$^+$m/z 1460.1 (n=10), 1548.1 (n=12), 1592.2 (n=13), 1636.2 (n=14), 1680.1 (n=15), 1724.0 (n=16), 1769.0 (n=17), 1812.9 (n=18); (M+NH$_4$)$^{2+}$m/z 871.3 (n=16), 893.5 (n=17), 915.5 (n=18), 937.0 (n=19), 959.4 (n=20), 981.4 (n=21).

What is claimed is:

1. A method of treating transplantation rejection or graft vs. host disease in a mammal in need thereof, which comprises administering to said mammal an antirejection effective amount of a compound of the structure

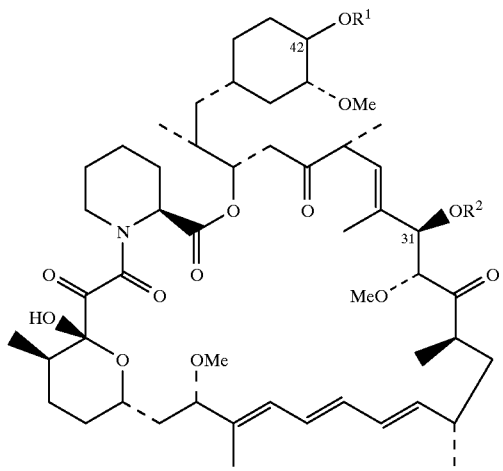

wherein R$^1$ and R$^2$ are each, independently, hydrogen or —COCH$_2$—S—CH$_2$CH$_2$—O—CH$_2$—(CH$_2$OCH$_2$)$_n$—CH$_2$—O—CH$_2$CH$_2$—OCH$_3$; and n=8–450; with the proviso that R$^1$ and R$^2$ are not both hydrogen.

2. A method of treating a fungal infection in a mammal in need thereof, which comprises administering to said mammal an antifungal effective amount of a compound of the structure

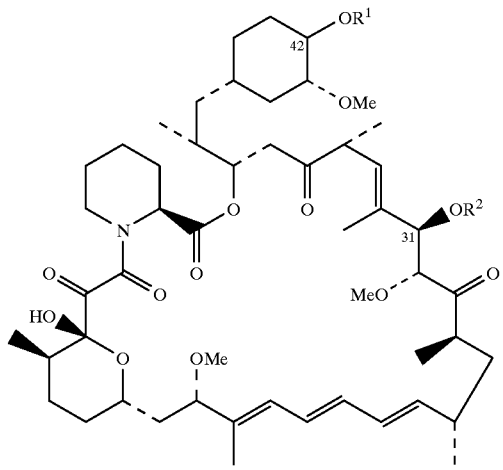

wherein R$^1$ and R$^2$ are each, independently, hydrogen or —COCH$_2$—S—CH$_2$CH$_2$—O—CH$_2$—(CH$_2$OCH$_2$)$_n$—CH$_2$—O—CH$_2$CH$_2$—OCH$_3$; and n=8–450; with the proviso that R$^1$ and R$^2$ are not both hydrogen.

3. A method of treating rheumatoid arthritis in a mammal in need thereof, which comprises administering to said mammal an antiarthritis effective amount of a compound of the structure

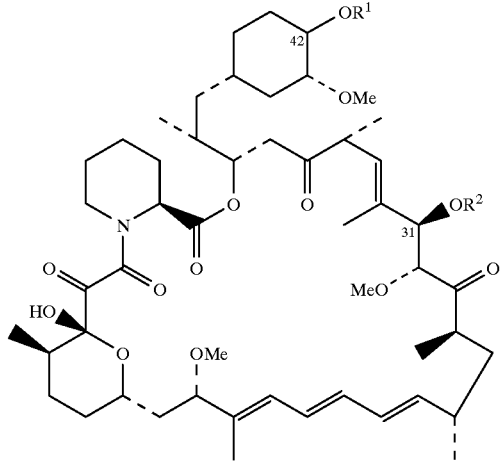

wherein R$^1$ and R$^2$ are each, independently, hydrogen or COCH$_2$—S—CH$_2$CH$_2$—O—CH$_2$—(CH$_2$OCH$_2$)$_n$—CH$_2$—O—CH$_2$CH$_2$—OCH$_3$; and n=8–450; with the proviso that R$^1$ and R$^2$ are not both hydrogen.

* * * * *